(12) United States Patent
Li et al.

(10) Patent No.: US 9,719,062 B1
(45) Date of Patent: Aug. 1, 2017

(54) GAS GENERATION

(71) Applicant: The Board of Regents of the University of Nebraska, Lincoln, NE (US)

(72) Inventors: Haorong Li, Omaha, NE (US); Daihong Yu, Omaha, NE (US); Yanshun Yu, Nanjing (CN)

(73) Assignee: NUTECH VENTURES, Lincoln, NE (US)

( * ) Notice: Subject to any disclaimer, the term of this patent is extended or adjusted under 35 U.S.C. 154(b) by 865 days.

(21) Appl. No.: 13/936,130

(22) Filed: Jul. 5, 2013

Related U.S. Application Data

(60) Provisional application No. 61/668,098, filed on Jul. 5, 2012.

(51) Int. Cl.
  *C12M 1/00* (2006.01)
  *C12M 3/00* (2006.01)
  *C12M 1/107* (2006.01)

(52) U.S. Cl.
  CPC ................... *C12M 21/04* (2013.01)

(58) Field of Classification Search
  CPC ........ G05D 11/003; G05D 7/03; G05D 11/04; C12M 21/04; C12M 23/58; C12M 27/06; C12M 41/12; C12M 41/22; C12M 41/40; C12M 45/02; C12M 45/20; C12M 47/14; C12M 47/18; C12M 47/20; B08B 15/02; F16L 55/00; Y10T 137/8593; Y02E 50/343; Y02W 30/47; Y02W 30/43; Y02W 10/37;
(Continued)

(56) References Cited

U.S. PATENT DOCUMENTS

2002/0079266 A1* 6/2002 Ainsworth ................ C02F 3/28
  210/603
2006/0138046 A1* 6/2006 Stafford .................. C02F 1/441
  210/605
(Continued)

OTHER PUBLICATIONS

G. Irvine, E. R. Lamont, and B. Antizar-Ladislao; Energy from Waste: Reuse of Compost Heat as a Source of Renewable Energy; International Journal of Chemical Engineering; vol. 2010, Article ID 627930; 10 pages.

*Primary Examiner* — William H Beisner
*Assistant Examiner* — Danielle Henkel
(74) *Attorney, Agent, or Firm* — Advent, LLP

(57) ABSTRACT

A first system includes a feedstock load port and a feedstock discharge port. The first system also includes a tank configured to retain biomass feedstock for aerobic biodegradation. The first system further includes a mechanical ventilator in fluid communication with the tank. The mechanical ventilator is configured to supply air to facilitate the aerobic biodegradation of the biomass feedstock. The first system also includes an exhaust port configured to receive gas generated during the aerobic biodegradation. A second system includes a feedstock load port and a feedstock discharge port. The second system also includes a pressure vessel configured to retain biomass feedstock for anaerobic biodegradation. The second system further includes a gas release device to facilitate migration of gas within the pressure vessel. The second system also includes a water cycler configured to cycle water within the pressure vessel. The second system further includes an exhaust port.

6 Claims, 5 Drawing Sheets

(58) Field of Classification Search
CPC ....... Y02W 10/23; Y02P 20/145; Y02P 20/59; C05F 17/0018; C02F 3/28; C02F 3/34; C02F 11/04; C02F 2103/20; C02F 2103/28; C02F 2209/02; C02F 2209/03; C02F 2209/42; C02F 2301/066
See application file for complete search history.

(56) References Cited

U.S. PATENT DOCUMENTS

| | | | |
|---|---|---|---|
| 2011/0236274 A1* | 9/2011 | Buchmueller | C02F 3/006 422/187 |
| 2014/0144531 A1* | 5/2014 | Hass | B08B 15/02 137/561 R |

* cited by examiner

GAS GENERATION

CROSS-REFERENCE TO RELATED APPLICATIONS

The present application claims the benefit under 35 U.S.C. §119(e) of U.S. Provisional Application Ser. No. 61/668,098, filed Jul. 5, 2012, and titled "Gas Collection System," which is herein incorporated by reference in its entirety.

BACKGROUND

As energy prices, environmental pollution, population growth, waste generation rate, and concerns regarding greenhouse-gas emissions continue to rise worldwide, there is an increasing desire for renewable energy and alternative energy and waste treatment solutions.

SUMMARY

A first system includes a feedstock load port and a feedstock discharge port. The first system also includes a tank configured to retain biomass feedstock for aerobic biodegradation. The first system further includes a mechanical ventilator in fluid communication with the tank. The mechanical ventilator is configured to supply air to facilitate the aerobic biodegradation of the biomass feedstock. The first system also includes an exhaust port configured to receive gas generated during the aerobic biodegradation and reclaim thermal heat energy continuously released during the aerobic biodegradation (e.g., for space heating, water heating, and so forth). In embodiments of the disclosure, water is cycled to enable a liquid rich condition for microbes. Additionally, temperatures of inlet and outlet air can be monitored for performance investigation and control purposes. Further, the first system can include multiple stages for scalable aerobic biodegradation. Additionally, one or more windows can be used to provide visibility of the biodegradation process. In embodiments, the first system is configured to aerobically degrade various liquid and solid biomass and biomass wastes.

A second system includes a feedstock load port and a feedstock discharge port. The second system also includes a pressure vessel configured to retain biomass feedstock for anaerobic biodegradation. The second system further includes a gas release device to facilitate migration of gas within the pressure vessel. The second system also includes a water cycler configured to cycle water within the pressure vessel. The second system further includes an exhaust port. In embodiments of the disclosure, the anaerobic biodegradation capacity of the second system is scalable. In some embodiments, the second system is configured to receive semi-compost from the first system. In other embodiments, the second system directly receives biomass feedstock with rich small monomers. The second system is configured to produce biogas energy and organic fertilizer quickly from various liquid and solid biomass and biomass wastes. The feedstock discharge port is configured to deliver the residue as, for example, organic fertilizer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

Figure 5:
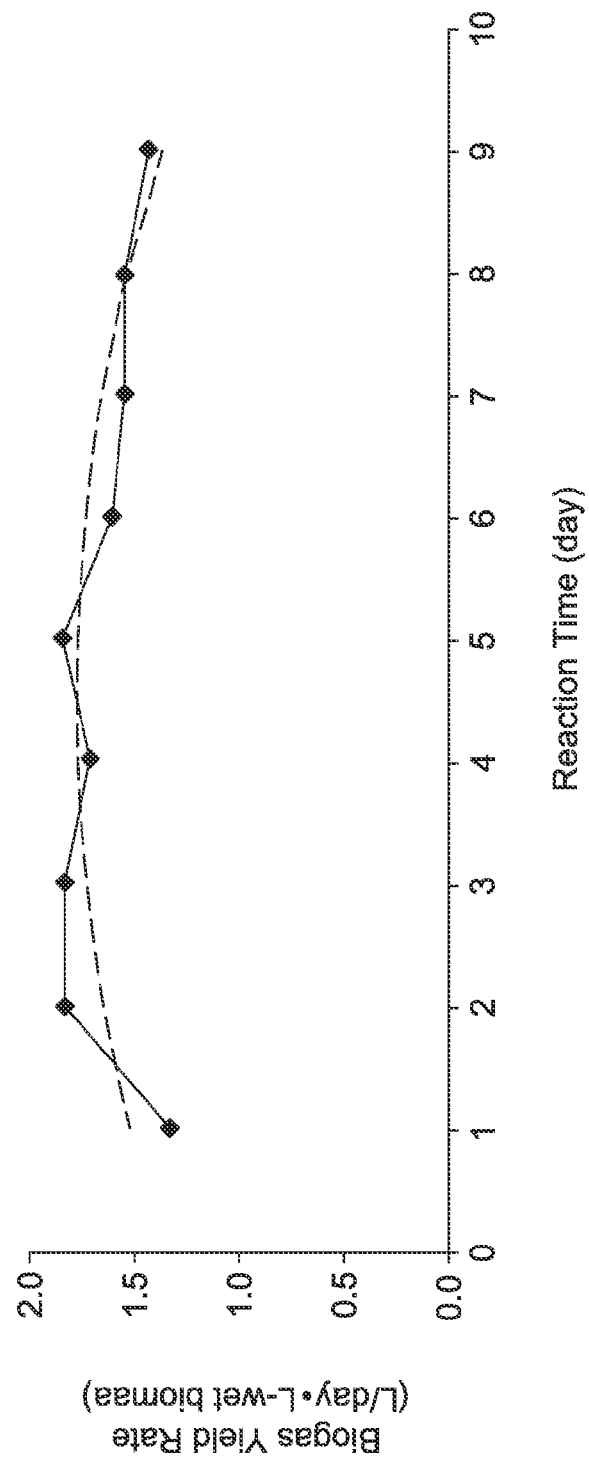

FIG. 5 is a graph illustrating results of anaerobic biodegradation, where an average biomass yield rate is approximately one and six-tenths liters per day of liter-wet biomass (1.6 L/day·L-wet biomass), a peak biomass yield rate is approximately one and eight-tenths liters per day of liter-wet biomass (1.8 L/day·L-wet biomass), a methane ($CH_4$) concentration is between approximately sixty-eight percent (68%) and seventy-five percent (75%), and a carbon dioxide ($CO_2$) concentration is between approximately twenty-four percent (24%) and thirty percent (30%) in accordance with an example embodiment of the present disclosure.

DETAILED DESCRIPTION

In 2009, more than two hundred and fifty (250) million tons of municipal solid waste (MSW) was generated. Over two-thirds of this waste was comprised of organic material. However, only about seven percent (7%) of the waste was composted to produce fertilizers and so forth. The majority of biomass waste is placed in landfills or incinerated. Biodegradation provides ecologically and/or environmentally friendly techniques for handling biomass solid wastes, such as organic MSW. For example, biomass biodegradation can reduce environmental effects of biomass wastes (e.g., by neutralizing carbon and/or reducing sulfur, nitrogen oxides, methane emissions, and so forth). Further, biodegradation of biomass solid waste can be used to produce bio-fertilizers, which can be used to promote healthy and fertile soils for improved agricultural productivity, food production, and so forth. Additionally, biogas generated during, for instance, anaerobic digestion of biomass can be used to provide heat and/or power. Still further, biodegradation can be used to conserve landfill space, reduce disposal costs of biomass waste, produce a useful end product, and so forth.

Referring generally to FIGS. 1A through 3, a system 100 for promoting the biodegradation of biomass, such as biomass solid waste, is described. The system 100 includes a feedstock load port 102 configured to receive biomass feedstock, and a feedstock discharge port 104 configured to discharge the biomass feedstock. The system 100 also includes a tank 106 disposed between the feedstock load port 102 and the feedstock discharge port 104. The tank 106 is configured to retain the biomass feedstock for aerobic biodegradation. The system 100 further includes a mechanical ventilator 108 (e.g., one or more fans) in fluid communication with the tank 106. The mechanical ventilator 108 is configured to supply air to facilitate the aerobic biodegradation of the biomass feedstock. For example, the system 100 includes an air supply grille 110 allowing the mechanical ventilator 108 to draw supply air into the system 100. The system 100 also includes an exhaust port 112 configured to receive gas (e.g., biogas) generated during the aerobic biodegradation of the biomass feedstock.

In some embodiments, the system 100 includes a controller 150 operatively coupled with the mechanical ventilator 108 to control the supply air temperature of the air. The controller 150 can also be operatively coupled with the mechanical ventilator 108 to control the supply air flow rate of the air. In embodiments of the disclosure, the system 100 includes a water cycler 114 configured to collect water proximate to the feedstock discharge port 104 and supply the water proximate to the feedstock load port 102. The controller 150 can be operatively coupled with the water cycler 114 to control the cycling of the water in the system 100. In some embodiments, the system 100 comprises one or more windows 116 disposed in the tank 106 for viewing the biomass feedstock in the tank (e.g., during biodegradation).

In embodiments of the disclosure, the system 100 includes multiple stages (e.g., a first stage 118, a second stage 120, a third stage 122, and so forth) for advancing the biomass feedstock during the aerobic biodegradation of the biomass feedstock in the tank 106. Further, access can be provided between the different stages using, for instance, a seal cap 124. In some embodiments, the system 100 includes a temperature sensor 126 coupled with the mechanical ventilator 108 for monitoring an inlet temperature associated with the air supplied to facilitate the aerobic biodegradation of the biomass feedstock. In some embodiments, the system 100 also includes a temperature sensor 126 coupled with the exhaust port 112 for monitoring an outlet temperature associated with the gas generated during the aerobic biodegradation of the biomass feedstock.

A system 100, including some or all of its components, can operate under computer control. For example, a processor 152 can be included with or in the controller 150 to control the components and functions of systems 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor 152 provides processing functionality for the system 100 and can include any number of processors, micro-controllers, or other processing systems, and resident or external memory for storing data and other information accessed or generated by the system 100. The processor 152 can execute one or more software programs that implement techniques described herein. The processor 152 is not limited by the materials from which it is formed or the processing mechanisms employed therein and, as such, can be implemented via semiconductor(s) and/or transistors (e.g., using electronic integrated circuit (IC) components), and so forth.

The system 100 also includes a memory 154. The memory 154 is an example of tangible, computer-readable storage medium that provides storage functionality to store various data associated with operation of the system 100, such as software programs and/or code segments, or other data to instruct the processor 152, and possibly other components of the system 100, to perform the functionality described herein. Thus, the memory 154 can store data, such as a program of instructions for operating the system 100 (including its components), and so forth. It should be noted that while a single memory 154 is described, a wide variety of types and combinations of memory (e.g., tangible, non-transitory memory) can be employed. The memory 154 can be integral with the processor 152, can comprise stand-alone memory, or can be a combination of both. The memory 154 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 100 and/or the memory 154 can include removable integrated circuit card (ICC) memory, such as memory provided by a subscriber identity module (SIM) card, a universal subscriber identity module (USIM) card, a universal integrated circuit card (UICC), and so on.

The system 100 includes a communications interface 156. The communications interface 156 is operatively configured to communicate with components of the system 100. For example, the communications interface 156 can be configured to transmit data for storage in the system 100, retrieve data from storage in the system 100, and so forth. The communications interface 156 is also communicatively coupled with the processor 152 to facilitate data transfer between components of the system 100 and the processor 152 (e.g., for communicating inputs to the processor 152 received from a device communicatively coupled with the system 100). It should be noted that while the communications interface 156 is described as a component of a system 100, one or more components of the communications interface 156 can be implemented as external components communicatively coupled to the system 100 via a wired and/or wireless connection. The system 100 can also comprise and/or connect to one or more input/output (I/O) devices (e.g., via the communications interface 156) including, but not necessarily limited to: a display, a mouse, a touchpad, a keyboard, and so on.

The communications interface 156 and/or the processor 152 can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to be restrictive of the present disclosure. Further, the communications interface 156 can be configured to communicate with a single network or multiple networks across different access points.

There are large amounts of energy contained in wastes. For instance, gross calorific values (GCV) of kitchen wastes, papers, and garden wastes are approximately fifteen and seven-tenths gigajoules per ton (15.7 GJ/t), seventeen and four-tenths gigajoules per ton (17.4 GJ/t), and sixteen and one-tenth gigajoules per ton (16.1 GJ/t), respectively. In the United States, there were about thirty-two and nine-tenths million tons (32.9 M tons) of yard trimmings in 2008, representing about two hundred trillion British thermal units (200 trillion Btu) of heat energy. Aerobic biodegradation can be used for waste treatment and/or production of fertilizers from these organic materials.

However, current biomass waste aerobic biodegradation technologies are generally used only for producing fertilizers. A significant amount of green thermal energy generated from composting processes is neglected and discharged to the atmosphere. Meanwhile, the aerobic biodegradation rate is typically too slow to be effective. Optimized biomass waste composting processes are overlooked and not exploited to increase the biodegradation rate.

The systems 100 described herein provide fast, low-cost, scalable biomass waste aerobic biodegradation for producing sustainable heat energy and bio-fertilizers. In embodiments, multiple types of biomass wastes demonstrate that after reaction occurs less than eight (8) hours, a sustainable heat output between approximately fifteen and one-tenth watts per kilogram-wet biomass (15.1 W/kg-wet biomass) and twenty-four and three-tenths watts per kilogram-wet biomass (24.3 W/kg-wet biomass) are produced, and the exhaust air temperature remains as high as between approximately seventy-five degrees Celsius (75° C.) and eighty-five degrees Celsius (85° C.). Further, the systems 100 provide biodegradation approximately ten (10) to fifteen (15) times faster than that of typical aerobic biodegradation technologies. The systems 100 can provide significant green heat energy, improve organic waste management, quickly deliver healthy and fertile soil, and minimize the impacts of environmental pollution.

Usually, it takes up to a year for microorganisms to compost garden clippings aerobically. Aerobic biodegradation is an exothermic process that can be controlled on the basis of temperature feedback, but present technologies neglect the direct control of temperatures, airflow rates, water availability, and so forth. Optimal control of the biomass waste composting process is overlooked and not exploited to increase the biodegradation rate. As a result, biodegradation is slower, more resources are required to handle biomass wastes using typical aerobic degradation technology, and greater capital investment is required, while fertilizer production and energy outputs are relatively limited.

Thus, large amounts of heat energy contained in the free renewable resources of biomass wastes have long been neglected and fully discharged to the atmosphere during the aerobic biodegradation processes. The existing degradation technologies attempt to produce fertilizers only by a natural process, rather than optimizing the composting processes with temperature, air flow and microorganism control for both energy recovery and waste stabilization.

The systems 100 described herein provide fast, low-cost, scalable biomass waste aerobic biodegradation. Modular industrial components, possibly with multiple stages, are used throughout the systems 100 to provide market-leading performance, scalability and service integration.

In the systems 100, biomass feedstock is loaded from the top of the tank 106 and unloaded from the feedstock discharge port 104 at the bottom of the tank 106. Energetic aerobic biodegradation continuously consumes significant oxygen for microorganisms to transform biomass matter into carbon dioxide ($CO_2$) and water ($H_2O$), and release free green heat. Thus, mechanical ventilation with controlled supply air temperature and flow rate is provided to evenly furnish sufficient, appropriate amounts of oxygen to microorganisms in the tank 106. Further, air supply grilles 110 are provided in each stage to maximize ventilation reception.

Water is essential to all living organisms. However, water is lost during the aerobic biodegradation process when the water evaporates from the top of the tank 106 and percolates down to the bottom of the tank 106. Thus, in the systems 100 described herein, water is cycled for to enable a liquid rich condition for microbes. Temperatures of inlet and outlet air of the aerobic biodegradation systems 100 are monitored for performance investigation and control purposes. In addition, to observe the decreasing feedstock volume, multi-visible windows 116 are provided at one or more of the stages.

In an embodiment, four stages are used in a biodegradation system 100 with a biomass disposal capacity of ninety-two and four-tenths kilograms (92.4 kg) on a wet basis. The system 100 is used with biomass waste types including grass clippings, leaves, sawdust, and sludge. The biomass waste has a particle size of between approximately one-quarter (¼) inch and one (1) inch. The biomass waste has a mixture ratio of carbon-to-nitrogen (C:N) between approximately twenty-five (25) and thirty-five (35). The system 100 has a supply airflow rate of approximately five and five-tenths cubic feet per minute (5.5 cfm). The system 100 has a supply air temperature between approximately thirty degrees Celsius (30° C.) and forty degrees Celsius (40° C.). The system 100 has a supply air humidity of approximately seventy-five percent (75%). The system 100 uses a water content between approximately seventy percent (70%) and eighty percent (80%).

Improper particle size can detrimentally impact the biodegradation rate of biomass wastes. Large particle size provides a small surface area for microbial "access" to organic material to be decomposed. However, excessively small particle size can cause low porosity, impede the movement of oxygen ($O_2$) in and carbon dioxide ($CO_2$) and ammonia ($NH_3$) out, and slow the biodegradation.

Different organic wastes have different C:N ratios. For example, the C:N ratio of grass clippings is about 20:1, the C:N ratio of leaves is about 60:1, the C:N ratio of sawdust is about 325:1, and the C:N ratio of sludge is about 10:1. Microbes thrive under appropriate proportions of carbon-to-nitrogen. High C:N ratios lead to slow decomposition, and the reaction stops when useable carbon is consumed. However, if the C:N ratio is too low, a significant quantity of ammonia, which is toxic to microbes, can be generated, and the decomposition rate of the biomass waste will decrease.

To provide sufficient oxygen to microorganisms, a supply air flow rate of approximately five and five-tenths cubic feet per minute (5.5 cfm) is used with exhaust air having an oxygen content between approximately five percent (5%) and ten percent (10%).

Temperature has a self-limiting effect on microbial activity and the rate of degradation of organic materials. Temperatures above forty degrees Celsius (40° C.) can provide an optimal condition for activating thermophilic microbes. Mesophilic microbes are active in temperatures ranging between approximately ten degrees Celsius (10° C.) and forty degrees Celsius (40° C.).

Additionally, to maintain a liquid rich condition, the system 100 at least substantially continuously humidifies supply air to around seventy-five percent (75%), and water content of biomass feedstock is sustained between approximately seventy percent (70%) and eighty percent (80%) during the aerobic biodegradation process, e.g., by cycling the water percolated at the bottom of the energy system to the top at least substantially continuously.

Figure 1A:
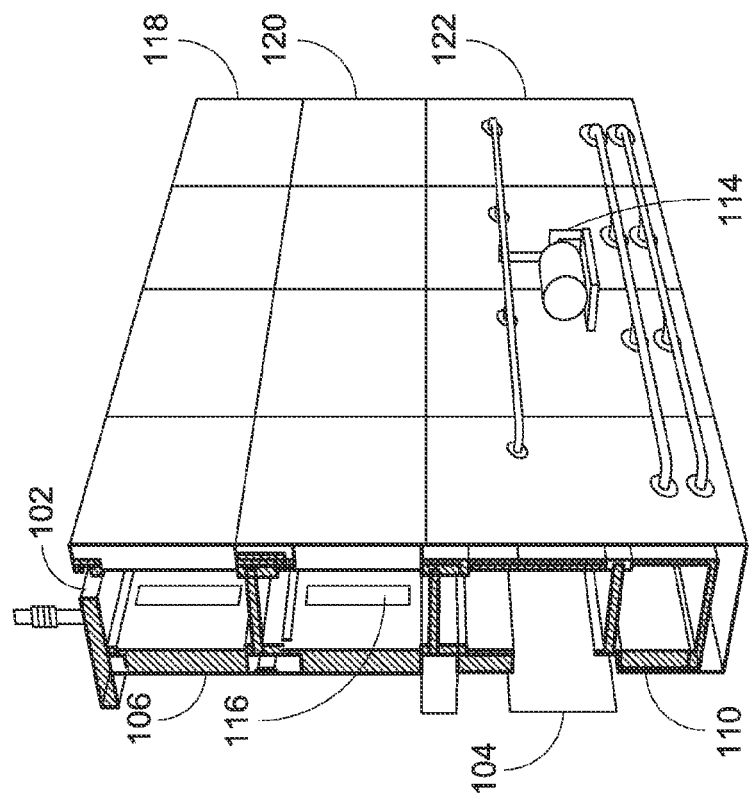
FIG. 1A is a front left perspective view illustrating an aerobic biodegradation system in accordance with example embodiments of the present disclosure.
Figure 1B:
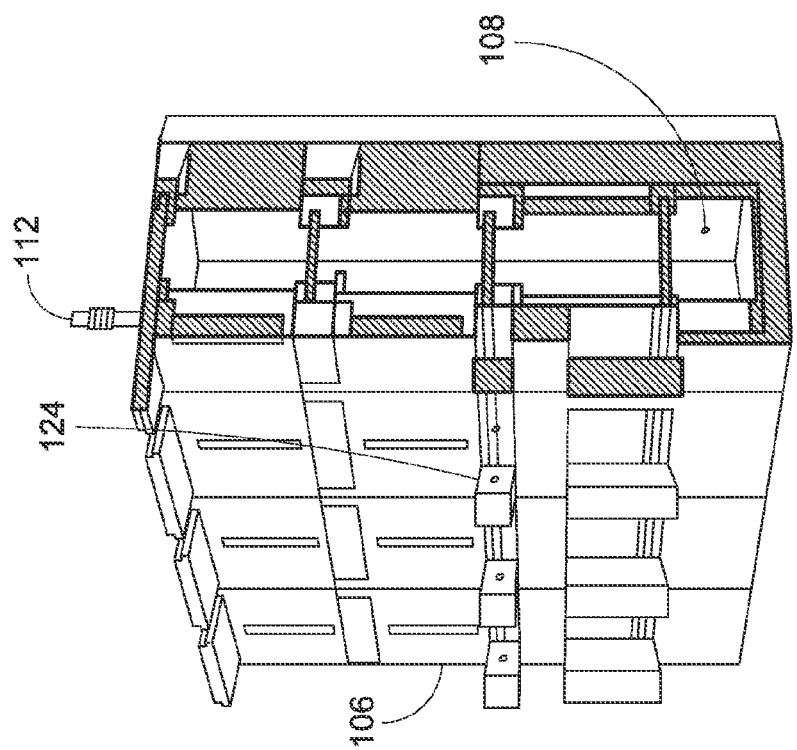
FIG. 1B is a rear left perspective view of the aerobic biodegradation system illustrated in FIG. 1A.
Figure 2:
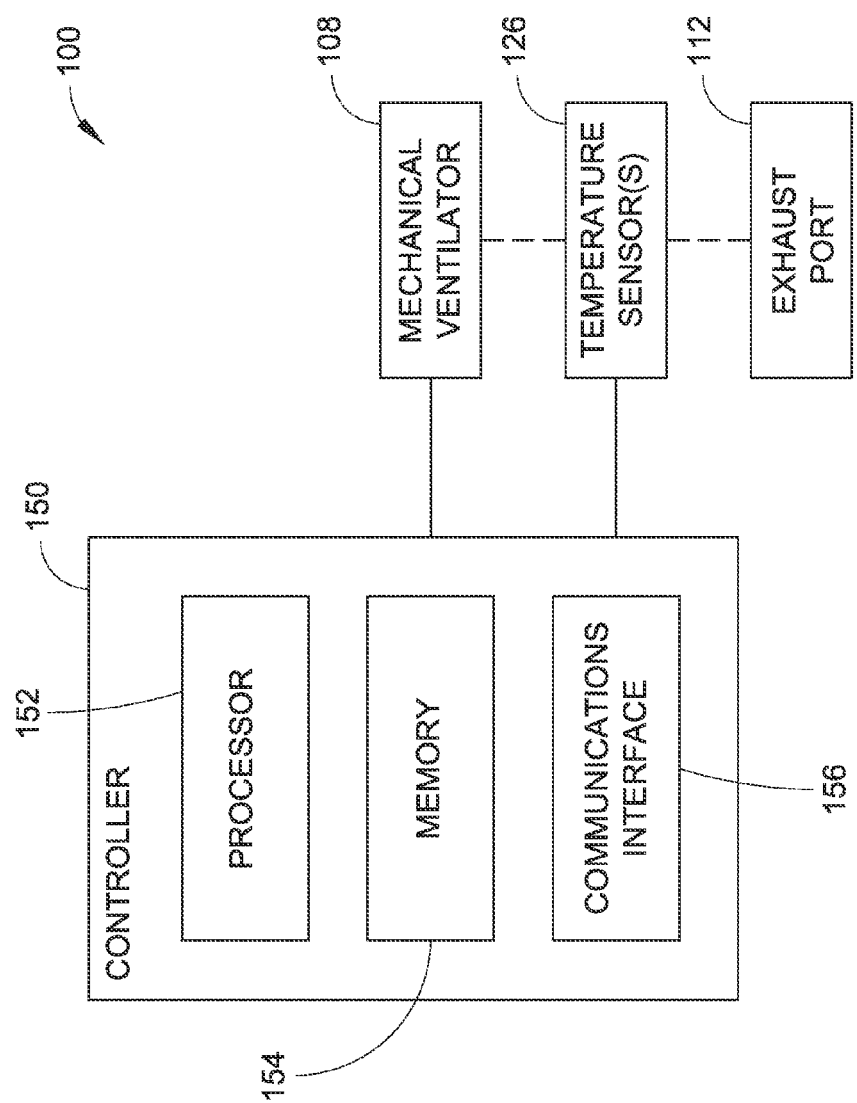
FIG. 2 is a block diagram illustrating a system including a controller operatively coupled with a mechanical ventilator and communicatively coupled with one or more temperature sensors in accordance with example embodiments of the present disclosure.
Figure 3:
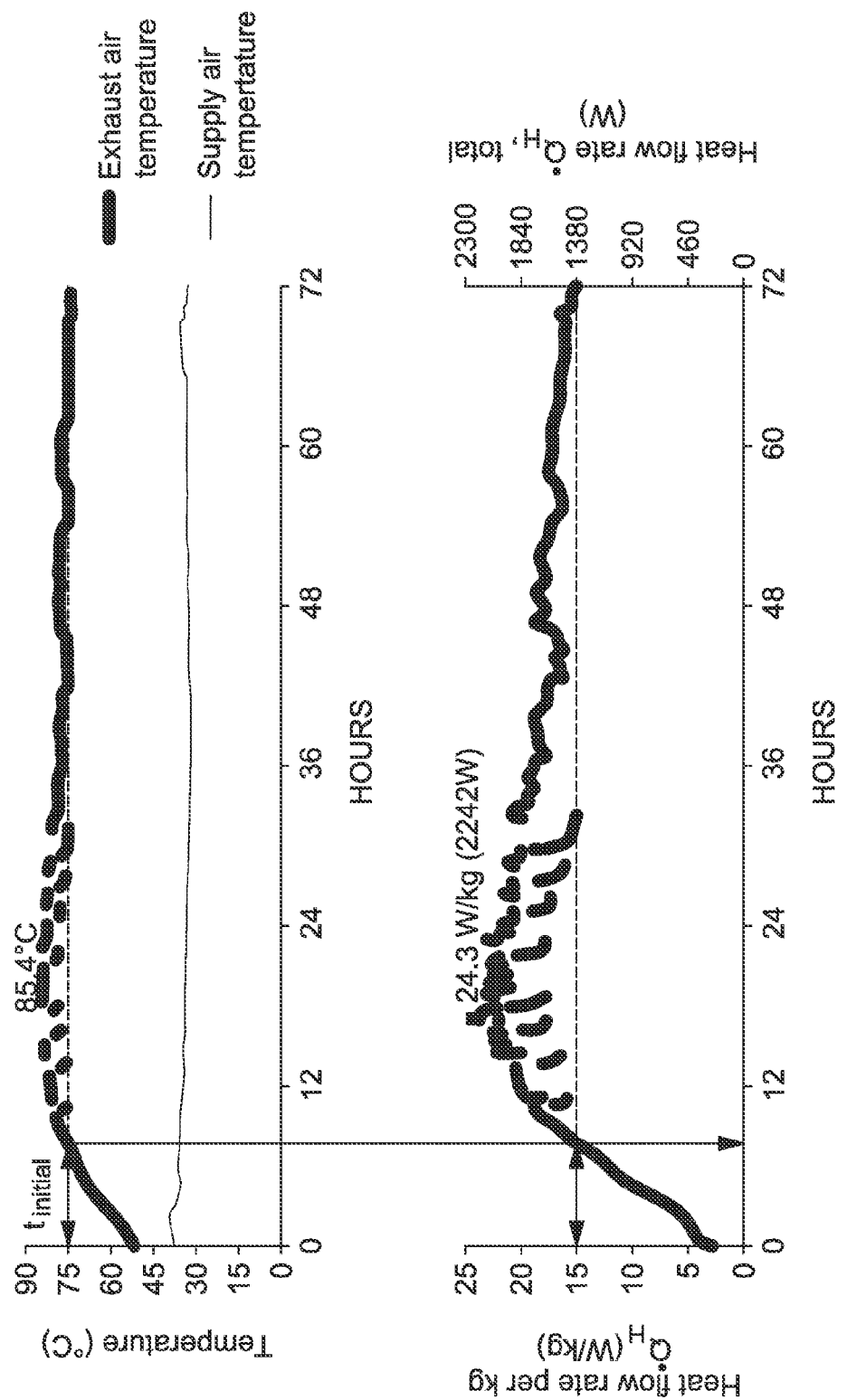
FIG. 3 is a graph illustrating results of aerobic biodegradation, where a daily energy generation on average is approximately forty and four-tenths kilowatt-hours per kilogram (40.4 kWh/kg) of wet biomass feedstock in accordance with an example embodiment of the present disclosure.

Referring to FIG. 3, a graph is provided that illustrates the results of aerobic biodegradation, where daily energy generation, on average, is approximately forty and four-tenths kilowatt-hours (40.4 kWh). The horizontal axis represents reaction duration in hours, and the vertical axes represent air temperature in Celsius degrees and heat flow rate in watts (W) or watts per kilogram (W/kg). After the reaction occurs less than eight (8) hours, the exhaust air temperature rises to seventy-five degrees Celsius (75° C.), with a temperature difference higher than forty degrees Celsius (40° C.), and the corresponding heat flow rate increases to fifteen and one-tenth watts per kilogram (15.1 W/kg). Then, within eighteen (18) hours, eighty-five and four-tenths degrees Celsius (85.4° C.) of peak exhaust air temperature was achieved, and the heat flow rate exceeded twenty-four and three-tenths watts per kilogram (24.3 W/kg), with a total heat flow rate of two thousand two hundred and twenty-four watts (2,242 W).

On average, the system 100 obtains a sustainable heat flow rate of eighteen and two-tenths watts per kilogram (18.2 W/kg), and daily energy generation is forty and four-tenths kilowatt-hours (40.4 kWh) for more than three (3) days. The heat flow rate of the system 100 is between approximately ten (10) and fifteen (15) times faster than typical aerobic biodegradation technologies, which have a heat flow rate between approximately one watt per kilogram (1 W/kg) and two watts per kilogram (2 W/kg) for approximately two (2) to five (5) months.

In this manner, systems 100 provide biomass waste aerobic biodegradation that produces sustainable heat energy and bio-fertilizers. The systems 100 are fast, low-cost, and scalable, and generate significant ecological, environmental, economic, and social benefits. For example, organic waste management can be improved in a cost-effective and fast manner; government financial expenses can be reduced for waste treatment; landfills and incineration can be limited; useful landfill space can be conserved; greenhouse gas emissions can be mitigated, and residual contaminants can be reduced; significant environmental benefits and sustainable development can be provided; dependency on fossil fuels and other costly renewable energy sources can be decreased; and green heat energy can be produced, directly reducing natural gas or electricity usage.

Using daily energy from aerobic biodegradation systems 100, daily domestic hot water needs of approximately four and one-tenth kilowatt-hours per day (4.1 kWh/day) for ten (10) households can be supported for more than three (3) days. The daily biomass waste generation of each household is approximately four kilograms (4.0 kg) in the United States. Using the daily generated biomass waste of these households, a biomass waste aerobic degradation system 100 can adequately reclaim thermal heat for hot water heating in homes.

With regards to fertilizer supply, healthy and fertile soil can be delivered for increased agricultural productivity and food production; soil and water resources can be conserved and enhanced, fragile wild lands and native ecosystems can be protected; and the extensive use of chemical fertilizer and various insecticides can be avoided, improving food quality.

Figure 4:
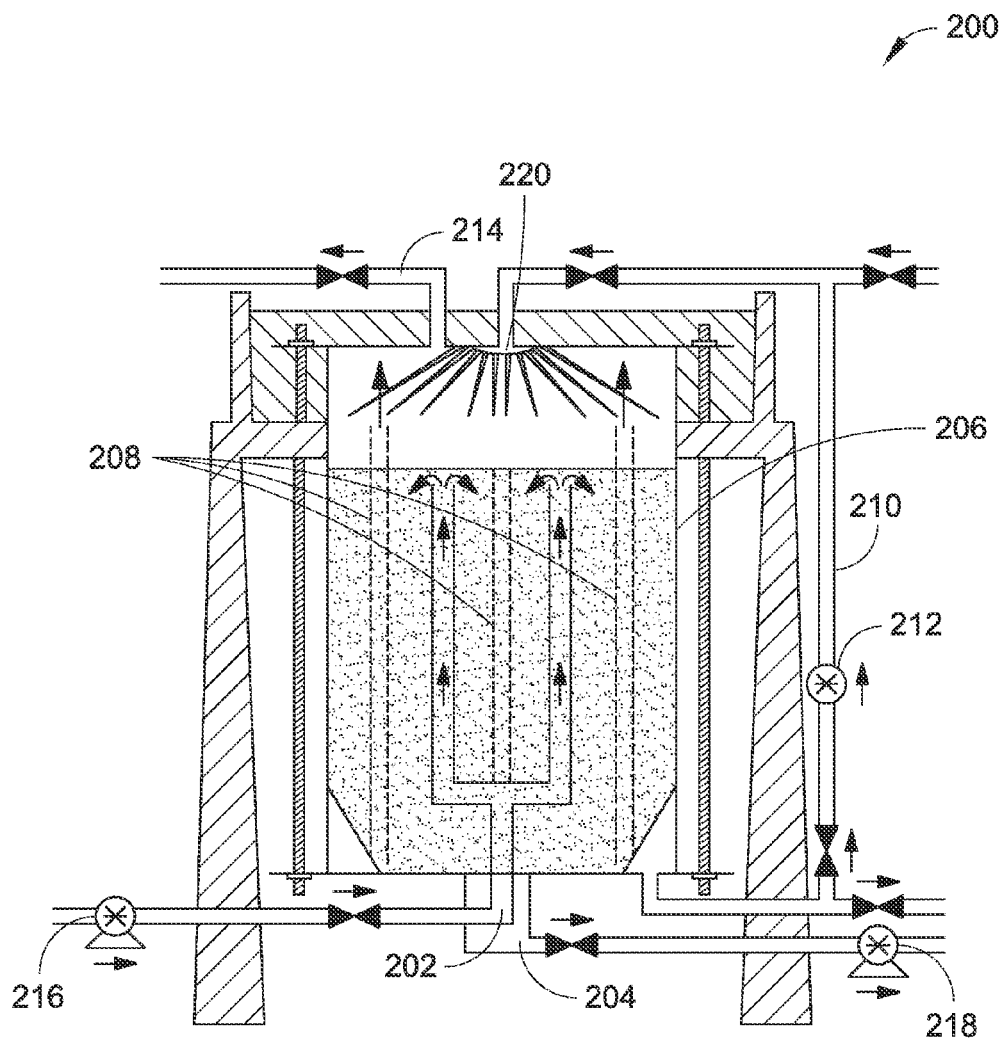
FIG. 4 is a partial cross-sectional side elevation view illustrating an anaerobic biodegradation system in accordance with example embodiments of the present disclosure.

Referring generally to FIGS. 4 and 5, a system 200 for promoting the biodegradation of biomass, such as biomass solid waste, is described. The system 200 includes a feedstock load port 202 configured to receive biomass feedstock (e.g., aerobically pretreated biomass feedstock from the system 100), and a feedstock discharge port 204 configured to discharge the biomass feedstock (e.g., as residuals for fertilizers and the like). The system 200 also includes a pressure vessel 206 (e.g., a water-sealing case) disposed of the feedstock load port 202 and the feedstock discharge port 204. The pressure vessel 206 is configured to retain the biomass feedstock for anaerobic biodegradation. The system 200 further includes one or more gas release devices 208 (e.g., gas release tubes) disposed within the pressure vessel 206 to facilitate migration of gas (e.g., biogas) generated during the anaerobic biodegradation of the biomass feedstock within the pressure vessel 206 (e.g., upwards towards the top of the pressure vessel 206). The system 200 also includes a water cycler 210 configured to cycle water within the pressure vessel 206. For instance, the water cycler 210 is configured to collect water proximate to the bottom of the pressure vessel 206 and supply the water proximate to the top of the pressure vessel 206 (e.g., using a water pump 212 or the like). The system 200 further includes an exhaust port 214 configured to receive gas (e.g., biogas) generated during the anaerobic biodegradation of the biomass feedstock.

In some embodiments, the system 200 includes a slurry pump 216 for pumping the biomass feedstock to the feedstock load port 202. In some embodiments, the system 200 includes a slurry pump 218 for pumping the biomass feedstock from the feedstock discharge port 204. In embodiments of the disclosure, the system 200 includes a water dispersal assembly 220 disposed proximate to the top of the pressure vessel 206. For example, the water dispersal assembly 220 can be configured as an array of nozzles, apertures, tubes, and the like configured to spray water over a top surface of the biomass feedstock.

Aerobic biodegradation is an environmentally friendly and cost effective method to handle biomass waste. For example, as discussed above, systems 100 provide fast, low-cost, scalable aerobic biodegradation for rapid disposal of biomass waste, delivery of fertile soils, and production of heat energy. Anaerobic biodegradation by microorganisms in the absence of oxygen is also a sustainable method to break down biomass waste to provide healthy fertilizers, conserve landfill space, and reduce disposal cost. The energy end-product of anaerobic digestion is biogas, which can be used for both heat and power. However, typical biomass waste anaerobic biodegradation technologies still have deficiencies. For example, typical anaerobic biodegradation technologies are too slow to be effective. In some instances, a retention time of at least two months is required. Further, these technologies primarily use limited sources of biomass, e.g., animal manure and sewage sludge. Moreover, typical biomass pretreatment methods are often costly and problematic.

The systems 200 provide fast, low-cost, scalable biomass waste anaerobic degradation for producing sustainable biogas energy and bio-fertilizers. In embodiments of the disclosure, the systems 200 use fast aerobic biodegradation technology as a pretreatment method to effectively break down the most complex compounds of biomass waste to readily biodegradable products and significantly increase the anaerobic biodegradation rate. For example, in some embodiments one or more systems 100 comprising a first stage of a biomass biodegradation system are coupled with one or more systems 200 comprising a second stage of a biomass biodegradation system. In some embodiments, multiple types of biomass wastes are used to provide a sustainable biogas yield rate of between approximately one and forty one-hundredths liters per day of liter-wet biomass (1.40 L/day·L-wet biomass) and one and eighty one-hundredths liters per day of liter-wet biomass (1.80 L/day·L-wet biomass). In embodiments of the disclosure, the systems 200 are at least approximately three (3) times faster than typical anaerobic biodegradation technologies. Systems 200 can generate significant biogas energy for heat and power, directly reduce natural gas or electricity usage, minimize capital investment, reduce resources usage for biogas energy plants, improve organic waste management, and deliver healthy and fertile slurry.

Anaerobic biodegradation is an environmentally and ecologically friendly method to handle biomass solid wastes by minimizing environmental effects including neutralizing carbon; significantly reducing sulfur, nitrogen oxides, and methane emissions; and delivering healthy and fertile soils for better agricultural productivity and food production. Further, anaerobic biodegradation conserves landfill space and reduces disposal cost. The most significant energy driven process on the Earth with respect to ecosystems is that of photosynthesis, which converts light into a form of potential energy held in the chemical bonds within organic matter. After that, the natural, biological, exothermal process, anaerobic biodegradation, can transform putrescible organic matter using microorganisms into carbon dioxide ($CO_2$) and water ($H_2O$), and continuously release the free fuel of biogas energy.

Current biomass pretreatment methods are often costly and problematic. For instance, high pressures ranging from six hundred kilopascals (600 kPa) to two thousand five hundred kilopascals (2,500 kPa) with accompanying heat treatments generally in a range between one hundred fifty degrees Celsius (150° C.) and two hundred degrees Celsius (200° C.) have been used. These treatments are regarded as an effective pretreatment method. However, high pressure treatment using highly sophisticated devices is very costly, and thermal pre-treatment also requires the input of a considerable amount of heat, which consumes a significant part of the produced biogas. Further, such methods can only disrupt relatively big particulate organic matter to small particles and enhance the solubility of the cell components to a certain extent. More effective methods to fundamentally break down the most complex organic matter to readily biodegradable compounds and increase the biodegradation rate are needed to improve anaerobic biodegradation technology.

Systems 200 are described that reclaim the free green biogas energy from biomass waste using anaerobic biodegradation technology in an effective manner, fast, low-cost, scalable manner. As shown in FIG. 4, the pressure vessel 206 (e.g., a cylindrical reactor) uses modular industrial components to ensure market-leading performance, scalability and service integration.

Aerobically pre-treated biomass feedstock with rich biodegradable compounds is loaded automatically and periodically to the top of the anaerobic biodegradation system 200 using, for instance, the slurry pump 216. The residuals, which can be processed as natural bio-fertilizers are unloaded from the bottom of the anaerobic biodegradation system 200 using, for example, the slurry pump 218. To enable an anaerobic environment for microorganisms to energetically digest the pretreated biomass materials, an economic, high-pressure water-sealing case is built on the top of the energy system. Inner gas release devices 208 (e.g., biogas release tubes) with large surface areas are also provided to allow high biogas release efficiency and further promote and accelerate the anaerobic biodegradation.

Water is essential to all living organisms. To create a liquid rich condition for the microorganisms but avoid the majority of feedstock fully being immersed under the water, the fertile discharge percolated down to the bottom of the anaerobic biodegradation system with a plentiful store of bacteria and minor organic components is collected and recycled by pumping the discharge to the top of the pressure vessel 206 and continuously permeating the discharge into the biomass feedstock.

In some embodiments, biomass mixtures are pretreated using a fast aerobic biodegradation technology, which breaks down most complex organic matters to readily biodegradable compounds, directly bypassing a hydrolysis stage, and stabilizing the feedstock to produce an energy-rich biogas in a fast and cost-effective manner. For example, a disposal capacity of fifty two (52.0) liters biomass waste on a wet basis after an aerobic pre-treatment is used in the anaerobic biodegradation system 200.

Temperature has a self-limiting effect on microbial activity and the rate of degradation of organic materials. There are three temperature ranges during which different types of microbes can be activated: psychrophilic at between approximately five degrees Celsius (5.0° C.) and fifteen degrees Celsius (15.0° C.), mesophilic at between approximately thirty-five degrees Celsius (35.0° C.) and forty degrees Celsius (40.0° C.), and thermophilic at between approximately fifty degrees Celsius (50.0° C.) and fifty-five degrees Celsius (55.0° C.). Anaerobes are most active in the mesophilic and thermophilic temperature ranges. A relatively high operating temperature has several benefits including an increasing solubility of organic compounds and growth rate of microorganisms, enhanced biological and chemical reaction rates, and an increased death rate of pathogens (e.g., in the thermophilic temperature range). However, microorganisms are very sensitive to sudden thermal changes, and reaction failure can occur at temperature changes in excess of one degree Celsius per day (1.0° C./day). The control of high operating temperatures for thermophilic biodegradation is very sensitive as compared to mesophilic biodegradation. In some embodiments, temperatures of the anaerobic reaction are maintained in a range between approximately thirty-seven degrees Celsius (37.0° C.) and thirty-nine degrees Celsius (39.0° C.).

Water is essential to all living organisms. High water containing substrates not only unnecessarily increase the system volume, but also raise the heat input per liter biomass waste required, resulting in unfavorable process economics. High total solid contents (TSs) dramatically change the fluid dynamics of substrates, often causing process failure due to bad mixing behavior, solids sedimentation, clogging, and scum layer formation. To maintain a liquid-rich condition, in some embodiments the TSs are stabilized in a range between approximately ten percent (10%) and fifteen percent (15%).

PH value is also an important parameter affecting the growth of microbes during the anaerobic biodegradation. In some embodiments, the PH ranges between six and five-tenths (6.5) and seven and five-tenths (7.5).

Referring to FIG. 5, a graph is provided that illustrates the results of anaerobic biodegradation. The horizontal axis represents reaction duration in days, and the vertical axis represents biogas yield rate in liters per liter of biomass waste on a wet basis. As shown, the reaction occurs quickly and reaches one and four-tenths liters per day of liter-wet biomass (1.4 L/day·L-wet biomass) in the first twenty-four (24) hours. In the following two (2) to four (4) days, the temperature increases to a peak biogas yield rate of one and eight-tenths liters per day of liter-wet biomass (1.8 L/day·L-wet biomass). On average, a sustainable biogas yield rate as high as one and six-tenths liters per day of liter-wet biomass (1.6 L/day·L-wet biomass) is provided for at least eight (8) days, with between approximately sixty-eight percent (68%) and seventy-five percent (75%) methane ($CH_4$) concentration and an additional content of between approximately twenty-four percent (24%) and thirty percent (30%) carbon dioxide ($CO_2$), which is at least three (3) times greater than typical anaerobic biodegradation technologies. In this manner, the biomass waste anaerobic degradation energy systems 200 can rapidly dispose of biomass waste and reclaim free biogas energy.

In embodiments of the disclosure, the systems 200 provide biomass waste anaerobic biodegradation that produces sustainable biogas energy and bio-fertilizers. The systems 200 are fast, low-cost, and scalable, and generate significant ecological, environmental, economic, and social benefits. For example, organic waste management can be improved in a cost-effective and fast manner; government financial expenses can be reduced for waste treatment; landfills and incineration can be limited; useful landfill space can be conserved; greenhouse gas emissions can be mitigated, and residual contaminants can be reduced; and significant environmental benefits and sustainable development can be provided. Further, green biogas energy for heat and power can be rapidly produced; natural gas or electricity usage can be reduced; dependency on fossil fuels and other costly renewable energy sources can be decreased; and capital investment and resources usage can be significantly reduced or minimized for biogas energy plants.

With regards to fertilizer supply, healthy and fertile soil can be delivered for increased agricultural productivity and food production; soil and water resources can be conserved and enhanced, fragile wild lands and native ecosystems can be protected; and the extensive use of chemical fertilizers and various insecticides can be avoided, improving food quality.

A system 200, including some or all of its components, can operate under computer control. For example, a processor can be included with or in a controller to control the components and functions of systems 200 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 200. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor provides processing functionality for the system 200 and can include any number of processors, micro-controllers, or other processing systems, and resident or external memory for storing data and other information accessed or generated by the system 200. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The system 200 also includes a memory. The memory is an example of tangible, computer-readable storage medium that provides storage functionality to store various data associated with operation of the system 200, such as software programs and/or code segments, or other data to instruct the processor, and possibly other components of the system 200, to perform the functionality described herein. Thus, the memory can store data, such as a program of instructions for operating the system 200 (including its components), and so forth. It should be noted that while a single memory is described, a wide variety of types and combinations of memory (e.g., tangible, non-transitory memory) can be employed. The memory can be integral with the processor, can comprise stand-alone memory, or can be a combination of both. The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 200 and/or the memory can include removable integrated circuit card (ICC) memory, such as memory provided by a subscriber identity module (SIM) card, a universal subscriber identity module (USIM) card, a universal integrated circuit card (UICC), and so on.

The system 200 includes a communications interface. The communications interface is operatively configured to communicate with components of the system 200. For example, the communications interface can be configured to transmit data for storage in the system 200, retrieve data from storage in the system 200, and so forth. The communications interface is also communicatively coupled with the processor to facilitate data transfer between components of the system 200 and the processor (e.g., for communicating inputs to the processor received from a device communicatively coupled with the system 200). It should be noted that while the communications interface is described as a component of a system 200, one or more components of the communications interface can be implemented as external components communicatively coupled to the system 200 via a wired and/or wireless connection. The system 200 can also comprise and/or connect to one or more input/output (I/O) devices (e.g., via the communications interface) including, but not necessarily limited to: a display, a mouse, a touchpad, a keyboard, and so on.

The communications interface and/or the processor can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to be restrictive of the present disclosure.

Further, the communications interface can be configured to communicate with a single network or multiple networks across different access points.

In embodiments of the disclosure, one or more systems 100 comprising a first stage of a biomass biodegradation system are coupled with one or more systems 200 comprising a second stage of a biomass biodegradation system. In this manner, a rapid two-stage waste biodegradation system for producing sustainable bio-heat, biogas, and/or bio-fertilizers is provided. The first stage implements a system 100 comprising a low-cost, scalable waste aerobic biodegradation system for quickly generating bio-heat and effectively pretreating biomass feedstock to readily anaerobically biodegradable products. The second stage implements a system 200 comprising a low-cost, scalable waste anaerobic biodegradation system using the residuals of the first stage for rapidly producing biogas and bio-fertilizers.

In embodiments of the disclosure, the first stage can obtain a sustainable heat recovery rate of between approximately fifteen watts per kilogram (15.0 W/kg) and eighteen and two-tenths watts per kilogram (18.2 W/kg), and between approximately fifty percent (50%) and ninety percent (90%) of the energy can be reclaimed in between approximately four (4) to six (6) days. Further, the second stage can obtain between approximately one and six-tenths liters (1.6 L) and one and eight-tenths liters (1.8 L) of biogas production per liter of wet biomass waste every day, and between approximately thirty percent (30%) and forty percent (40%) of energy contained in the aerobically pretreated wet biomass mixture can be recovered within ten (10) days.

With the combination of fast aerobic and anaerobic biodegradation processes, the majority of biomass energy can be reclaimed in around two (2) weeks. This rate is between approximately five (5) and ten (10) times faster than the rates of typical biodegradation technologies. Using the techniques described herein, a variety of benefits can be achieved, including generation of significant bioenergy for heat and power; saving limited, non-renewable fossil fuels; delivering healthy bio-fertilizers; recovering the carbon dioxide/oxygen ($CO_2/O_2$) cycle; saving useable land; and protecting and improving water and air quality. Further, the techniques described herein can be used to directly supply bio-heat energy for hot water and space heating in buildings and the like.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system or circuit. Further, elements of the blocks, systems, or circuits may be implemented across multiple integrated circuits. Such integrated circuits may comprise various integrated circuits including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block or circuit may be implemented using its software or firmware equivalent. In other instances, one part of a given system, block or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

The invention claimed is:

1. A system comprising:
   a feedstock load port configured to receive biomass feedstock;
   a feedstock discharge port configured to discharge the biomass feedstock;
   a pressure vessel disposed of the feedstock load port and the feedstock discharge port, the pressure vessel configured to retain the biomass feedstock for anaerobic biodegradation;
   a gas release device including a plurality of biogas release tubes disposed within the pressure vessel for facilitating migration of gas generated during the anaerobic biodegradation of the biomass feedstock within the pressure vessel from the biomass feedstock to the top of the pressure vessel, the biogas release tubes extending from proximate to the bottom of the pressure vessel to proximate to the top of the pressure vessel;
   a water cycler configured to collect water proximate to the bottom of the pressure vessel and supply the water to the top of the pressure vessel; and
   an exhaust port configured to receive the gas generated during the anaerobic biodegradation of the biomass feedstock.

2. The system as recited in claim 1, wherein the biomass feedstock supplied to the feedstock load port comprises aerobically pretreated biomass feedstock.

3. The system as recited in claim 1, further comprising a slurry pump for pumping the biomass feedstock to the feedstock load port.

4. The system as recited in claim 1, further comprising a slurry pump for pumping the biomass feedstock from the feedstock discharge port.

5. The system as recited in claim 1, further comprising a water dispersal assembly disposed proximate to the top of the pressure vessel.

6. The system as recited in claim 1, wherein the exhaust port is configured to receive the gas generated during the anaerobic biodegradation of the biomass feedstock at a rate of between approximately one and forty one-hundredths liters per day of liter-wet biomass and one and eighty one-hundredths liters per day of liter-wet biomass.

* * * * *